United States Patent [19]
Morgan

[11] 4,078,510
[45] Mar. 14, 1978

[54] RELATING TO THE CATHODIC PROTECTION OF STRUCTURES

[75] Inventor: John Harold Morgan, Winchester, England

[73] Assignee: Morgan Berkeley & Co. Ltd., Winchester, England

[21] Appl. No.: 757,735

[22] Filed: Jan. 7, 1977

[30] Foreign Application Priority Data

Jan. 12, 1976  United Kingdom ............... 01002/76

[51] Int. Cl.² ..................... G01R 31/02; B63H 25/00
[52] U.S. Cl. ............................... 114/144 A; 114/244; 324/52; 324/72; 340/4 E
[58] Field of Search ............. 114/144 A, 244; 324/72, 324/72.5, 52, 149, 51, 54; 340/3 T, 4 E, 248 A; 204/195 C, 195 F, 195 R

[56] References Cited

U.S. PATENT DOCUMENTS 3,526,831  9/1970  Smith ..................................... 324/52

FOREIGN PATENT DOCUMENTS 188,676  12/1922  United Kingdom .................... 324/3

Primary Examiner—Trygve M. Blix
Assistant Examiner—Reinhard J. Eisenzopf

[57] ABSTRACT

A method of surveying a cathodically protected metallic structure at least partly immersed in a liquid, such as an undersea pipeline which has sacrificial anodes attached at regular intervals along its length. The anodes provide a known electrolytic potential relative to the surrounding water. The potential differences in the water between a point adjacent an anode, and test points adjacent the pipeline are measured, and the varying level of protection along the pipe is determined from the variations between the measured potential differences.

14 Claims, 8 Drawing Figures

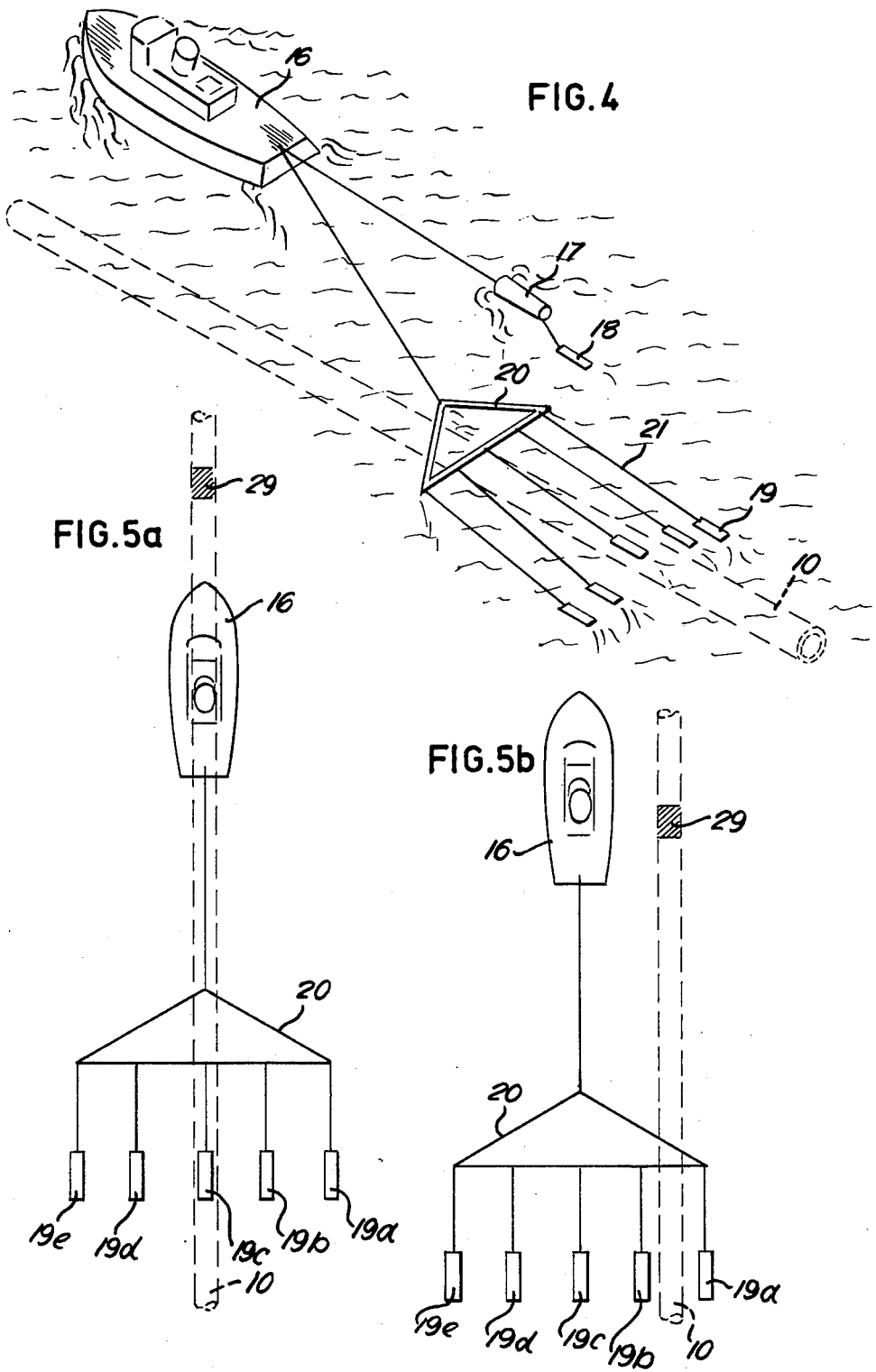

RELATING TO THE CATHODIC PROTECTION OF STRUCTURES

FIELD OF THE INVENTION

This invention relates to the cathodic protection of subaqueous structures, and more particularly to a method of checking the degree of protection afforded to a subaqueous structure by a cathodic protection system. The invention is particularly, but not exclusively concerned with the surveying of cathodically protected undersea pipelines.

BACKGROUND TO THE INVENTION

The cathodic protection from corrosion of a metallic structure which is at least partially immersed in a liquid involves depressing the potential of the structure so as to inhibit the anodic process of dissolution of the metallic atoms into the liquid as metal ions. This is commonly achieved by either one of two techniques, known as the impressed current technique, in which the structure is connected to the negative terminal of a d.c. power supply, and current passes through the liquid to the structure from one or more anodes connected to the positive terminal of the power supply; and the sacrificial anode technique, in which a number of blocks of metal less noble than that of the structure are attached to, and in electrical contact with the structure at various points. In the sacrificial anode technique, the metal of the anodes corrodes in preference to the metal of the structure, which becomes the cathode in the corrosion cell in which the liquid is the electrolyte, and consequently the anodes require replacing periodically.

The invention is particularly, but again not exclusively applicable to surveying a subaqueous structure protected by a sacrificial anode protection system.

An indication of the effectiveness of a cathodic protection system may be obtained by measuring the potential of the protected structure relative to the electrolytic liquid, and if the potential is above a predetermined "safe" level the current in an impressed current system is increased, whilst in a sacrificial anode system, the anodes which have become excessively worn and are no longer able to maintain the level of current flow necessary to depress the structure's potential sufficiently are replaced.

It is common practice, therefore, to monitor the potential of the structure to ensure that adequate protection is maintained, and since the protected structures are generally of considerable size, the potentials at not only one, but a number of points about the structure are monitored to ensure that all parts are properly protected. In many structures, such as ships' hulls, this monitoring is achieved relatively simply by means of cables connected permanently to various parts of the structure, and all leading to a central monitoring apparatus. However, such permanent connection is impracticable with structures to which access is limited, such as undersea pipelines.

DESCRIPTION OF THE PRIOR ART

FIG. 1 illustrates a known technique of measuring the surface potential of a pipeline 1 protected by a cathodic protection system utilizing the sacrificial anode technique, in which the anodes 2, only one of which is shown, are mounted on the pipe in electrical contact therewith at regularly spaced points along its length. The process of monitoring of the potential along the undersea pipeline employing this technique has necessitated a diver placing a probe 3 in direct electrical contact with the surface of the pipe at successive points spaced along its length, and measuring the potential at each point relative to a reference electrode 4 by means of a voltmeter 5.

Rarely is the surface of an undersea pipe sufficiently exposed to enable this operation to be carried out with efficiency, as the pipe may be encased in concrete or some other protective material, or may become covered in marine vegetation, necessitating the time consuming work of exposing the pipe surface before the direct contact and voltage reading can be made.

OBJECT OF THE INVENTION

The object of the present invention is to provide a method of carrying out a survey on a cathodically protected underwater structure which obviates the necessity of making direct electrical contact with the structure.

Where an undersea pipeline is protected by a sacrificial anode system, protective current flows from an anode through the seawater onto the pipe at a given point and through the metal of the pipe back to the anode. Assuming that there is no potential drop along that part of the pipe which completes protective circuit by which this given point on the pipe surface is protected, the voltage across the seawater between the anode and the given point will equal the difference between the voltages across the anode/sea interface, and the pipe/sea interface at that given point. Thus, if the voltage across the seawater and the voltage across the anode/sea interface are both known, the value of the voltage across the pipe/sea interface may be calculated.

SUMMARY OF THE INVENTION

According to the invention, therefore, there is provided a method of surveying a cathodically protected metallic structure at least partly immersed in a liquid, the metallic structure having electrically connected thereto a metallic element of known electrolytic potential relative to the liquid the method comprising determining the potential differences in the liquid between a point adjacent the metallic element, and test points adjacent the metallic structure, and determining the varying level of protection about the structure from the variations in the said potential differences.

Preferably, the method includes determining the potential of the pipe, at each of said various points, relative to the liquid by subtracting from the said known electrolytic potential, the corresponding value of said potential difference, and comparing the determined value of said potential with a predetermined value associated with minimum acceptable protection.

The method, when used in surveying an elongate underwater structure, such as a pipeline, having a plurality of said metallic elements connected thereto at spaced points along its length, may include placing a test electrode adjacent a said metallic element, moving a further test electrode in the liquid along the pipeline and monitoring the potential difference between the two test electrodes. Preferably, however, test electrode means are moved in the liquid along the pipeline, and the potential difference between the test electrode means, and a reference electrode remote from the pipeline is monitored.

The metallic elements are preferably the sacrificial anodes of a cathodic protection system; a peak in the potential difference between the test electrode means and the reference electrode occurs as the said test electrode means pass a sacrificial anode, and this peak value is used to determine, by subtraction, the required potential difference in the water as the test electrode means moves along the pipe.

The test electrode means and the reference electrode may be towed by a vessel moving on the surface of the water. The test electrode means may comprise a single test electrode but preferably comprise a plurality of test electrodes towed in parallel over the pipeline by the vessel and spaced apart transverse to the direction of travel of the vessel. The potentials of all of the test electrodes, relative to the reference electrode are monitored, and the position of the pipeline, relative to the electrodes may be determined, using these potentials, and the steering of the vessel may be compensated accordingly, to ensure that the vessel follows the route of the pipeline.

Some embodiments of the invention will now be described with reference to the accompanying drawings, in which:

FIG. 4 illustrates a further method, in accordance with the invention, of monitoring the protection of an undersea pipeline in which method a number of test electrodes are towed in parallel along the pipeline;

FIGS. 5a and 5b are schematic plans showing test electrodes using in the method of FIG. 4 in different positions relative to the pipeline;

Figure 1:
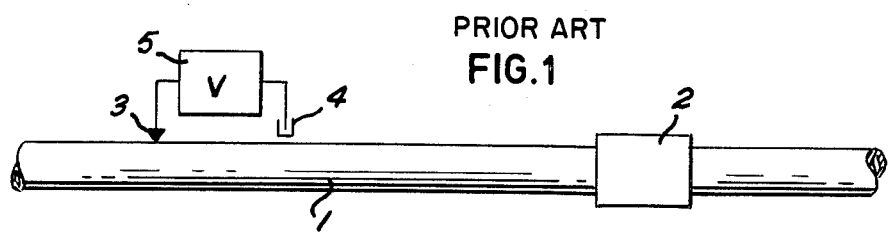
FIG. 1 illustrates a conventional method of measuring the potential of a cathodically protected undersea pipeline.

When an undersea ferrous pipe is protected by sacrificial anodes, the protection current flowing between the anodes and the pipe causes polarization at the surface of the pipe and it is the polarization potential at the surface of the pipe, that is, the voltage across the pipe/seawater interface which is to be measured to give an indication of the degree of cathodic protection. As mentioned above, the conventional method illustrated in FIG. 1 of measuring the pipe potential involves making a metal-to-metal contact between a probe and the pipe itself.

DESCRIPTION OF THE PREFERRED EMBODIMENTS

Figure 2:
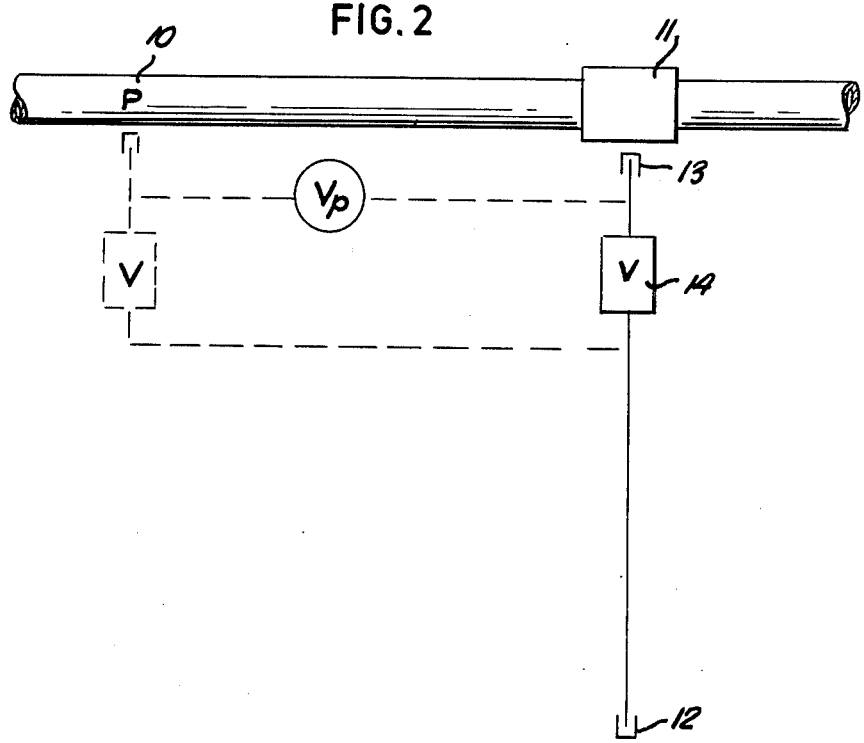
FIG. 2 illustrates a method in accordance with the invention.

With reference to FIG. 2, a pipeline 10 which is being surveyed is cathodically protected by a system including sacrificial anodes 11 of which only one is shown in the figure. These anodes may for instance comprise zinc bracelets which encircle the pipeline, and may be spaced at regular intervals of, say 100 ft. A survey system includes a remote reference electrode 12 which is maintained sufficiently remote from the pipeline to provide a constant reference potential which is unaffected by the protection system. In practice a distance in excess of 20 feet between the pipe and reference electrode is required. The system also includes a test electrode 13 and a voltmeter 14 arranged to indicate the potential of the test electrode 13 relative to the reference electrode 12. The test and reference electrodes may be of a well known silver/silver chloride, or zinc construction.

The test electrode is moved along the pipeline as close as possible to its surface, and its relative potential is monitored by means of the voltmeter. If this relative potential is measured when the test electrode is adjacent the anode 11 (in full lines) and then adjacent a point P (in broken lines) between the anode 11 and the next anode (not shown) along the line, one may, by subtraction obtain a value for the voltage $V_p$ across the seawater between the anode and point P on the pipe. Alternatively, the voltmeter could be connected between two test electrodes, one adjacent the anode, and the other adjacent point P, to obtain, by direct reading, a value for voltage $V_p$.

Figure 3:
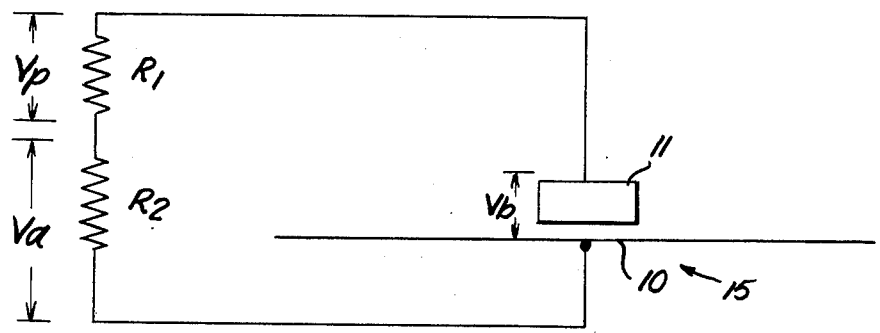
FIG. 3 illustrates a circuit which is electrically equivalent to a cathodic protection circuit and shows how, in accordance with the invention, the surface potential of an undersea pipeline may be monitored.

FIG. 3 illustrates how, knowing $V_p$ and one other parameter, it is possible to calculate the voltage across the pipe/sea interface at point P. FIG. 3 shows, as a simple electrical loop the circuit in which protection current flows, the source 15 of e.m.f. being the bimetallic couple comprising the pipe and anode in the seawater, and the two resistors $R_1$ and $R_2$ in the circuit representing respectively the resistance through the seawater between the anode and point P, and the effective resistance at the pipe/seawater boundary. $V_p$, as shown, is the measured voltage across the resistor $R_1$, and $V_a$ is the unknown voltage across $R_2$. The voltage $V_b$ across the seawater/anode interface, that is to say, the driving e.m.f. in the circuit-loop, is a known fundamental property of the sacrificial-anode material in seawater and in the case of zinc-anode on steel pipe is approximately 250mV. It is also known that for small currents flowing in the circuit voltage $V_b$ will not change appreciably. Consequently, the value of $V_p$ can be obtained by simply subtracting $V_a$ from $V_b$, thereby producing a reasonably accurate value for the relative potential of the pipe at point P without making direct contact with the pipe.

Where the survey is carried out by a diver, the purpose of the remote electrode 12 is to overcome the difficulties which he would experience in trying to measure directly the voltage $V_p$ between a test electrode adjacent the anode surface and another adjacent the pipe surface at point P which may be, for instance, 50 feet from the anode. By using a remote reference electrode which may, for example, by floating a hundred feet or so above him he could take the test electrode to the anode and, by means of the voltmeter 14 which would be of watertight construction, measure the potential at the anode surface relative to the reference electrode, and then measure the surface potential along the pipeline so enabling him to plot the potential change as he moves along the pipe. The area of least protection on the pipe is detected by a maximum plotted value for $V_p$, indicating a minimum value of the voltage $V_a$ across the pipe/seawater interface. When $V_p$ exceeds a predetermined maximum, it is known that the protection at the particular point on the pipe is unacceptably low.

Clearly, the direct measurement of $V_p$ would be practicable if the survey were to be carried out by two divers, as one diver would hold one test electrode at the anode, while the other diver would move the other test electrode along the pipe.

In a somewhat more efficient technique the voltage measurement of the survey is carried out at the surface. In this technique, a vessel moving on the surface of the water tows two electrodes, one of which is the reference electrode maintained remote from the pipeline, for instance suspended just below the water surface by means of a float, and the other of which is the test electrode which runs along the seabed adjacent, or over the pipe surface. Cables extend from the electrodes to monitoring apparatus on board the vessel, by which the potential difference between the two electrodes is monitored and recorded, the variations in this potential difference giving the varying value of $V_p$, from which $V_a$ is obtained, as explained hereinbefore.

Figure 6:
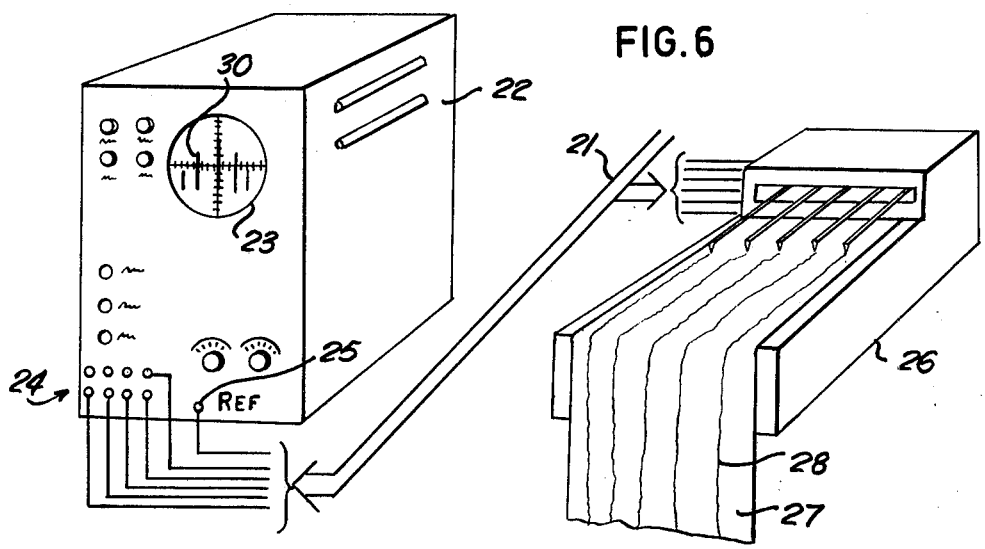
FIG. 6 illustrates monitoring and recording apparatus.

The problem with this technique is the difficulty in maintaining the test electrode sufficiently close to the pipeline to ensure that the values of $V_p$ obtained are reasonably accurate, without having a diver, or someone in a minisub following the test electrode and sending steering instructions to the surface vessel. It is suggested, therefore, that a technique as illustrated in FIG. 4 be employed. The survey surface vessel 16 tows a float 17 from which a reference electrode 18 is suspended so as to remain just underneath the surface, as before. However, instead of a single test electrode, a series of test electrodes 19 are towed in parallel over the pipeline 10. The electrodes 19 are equally spaced transverse to the direction of travel of the vessel, and are dragged across the seabed by means of a yoke 20 towed by the vessel, in a manner similar to a tractor towing a harrow, along the length of the pipeline. Each electrode is electrically coupled to one end of a respective conductor cable, these cables 21 extending to a monitoring apparatus aboard the vessel. This monitoring apparatus conveniently comprises a cathode ray oscilloscope 22 (FIG. 6) on the screen 23 of which the potentials measured by the test electrodes 19 and supplied to inputs 24 relative to the potential provided by the remote reference electrode 18 and supplied to reference input 25, may be displayed simultaneously in analogue form. These relative potentials are preferably also recorded in permanent form by means of, for example, a multiple pen recorder 26, which produces an elongate chart 27 bearing a different trace 28 of the time-varying relative potential for each respective test electrode. This permanent record enables on-shore analysis of the results, subsequent to completion of the survey, to provide an accurate, fully checked survey report.

Figure 7:
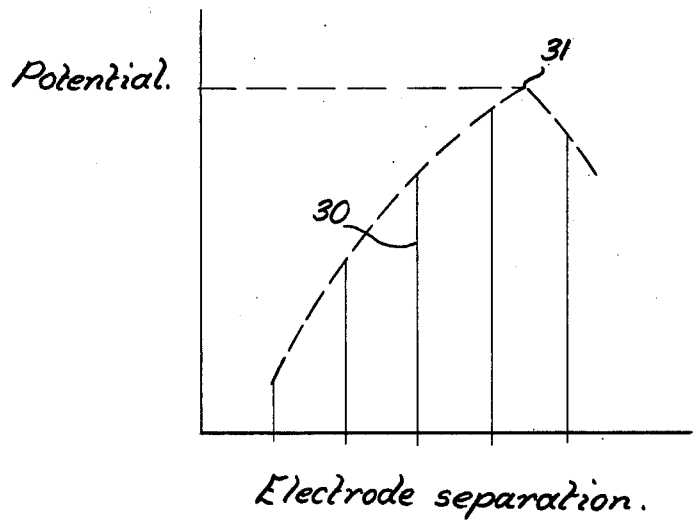
FIG. 7 is a graph illustrating the potentials obtained from test electrodes positioned as in FIG. 5b.

The technique illustrated in FIG. 4 utilizes five electrodes, and these are shown in FIG. 5a with the centre electrode 19c directly over the pipeline, and two electrodes each side of the pipeline. When the electrodes 19 pass an anode 29, a change in potential (relative to the reference electrode) will be registered by all of the electrodes 19, and displayed on screen 23, the central electrode 19c having the greatest potential change. Where, as in FIG. 5a, the central electrode 19c is directly over the pipe, this electrode will give the values of anode and pipe surface potential for calculation of $V_p$. However, in general, the electrodes 19 will not be towed symmetrically about the pipe, and at a given instant, the electrodes may be in the positions shown by way of example in FIG. 5b, with the pipeline between electrodes 19a and 19b, and closer to 19b. The electrode 19b will then register the greatest potential change as the test electrodes pass an anode, but it is not close enough to the pipeline to provide readings for obtaining an accurate value for $V_p$. However, by displaying the values of relative potential of all five electrodes as equally spaced vertical lines 30 on the screen 23, it will be possible to extrapolate the curve of potential against electrode position as defined by the tips of the lines 30, and illustrated in FIG. 7 so as to estimate the position relative to the test electrodes, and value of the maximum value of relative potential at any time. In the example shown in FIG. 7, which illustrates the form of curve of potential against electrode position which would be obtained if the electrodes were in positions relative to the pipe as shown in FIG. 5b, the extrapolated peak 31 of the curve occurs between the lines associated with electrodes 19a and 19b, and the abscissa and ordinate of this peak provide indications of the position of the pipe and the potential at the pipe surface respectively. As the electrodes 19 pass an anode, their relative potentials all reach a maximum, and the extrapolated peak defined at this instant represents the value of potential from which subsequent peak values (representing relative pipe surface potentials between successive anodes) are subtracted to determine $V_p$. The persistence of the screen 23 is adjusted to provide a lasting visual indication of this anode peak for comparison with the instantaneous changing pipe peak, so that $V_p$ can be continuously monitored.

The trawl of the electrodes 19 can be manoeuvered to correct any drift of the electrodes away from the pipeline, and in particular to return them to such positions that the electrode 19c is over the pipeline. This manoeuvring can most easily be achieved by simply steering the vessel 16 to correct any displacement of the extrapolated peak 31 on the CRO screen 23 from the vertical line associated with electrode 19c. For example, the situation illustrated in FIGS. 5b to 7 requires corrective steering of vessel 16 to starboard. It will be appreciated that the approximate location of the vessel along the pipeline is provided by a count of the peaks observed on the CRO, the spacing of the anodes 29 and point of commencement of the survey being known.

Thus, utilizing this technique of correction and continuous monitoring it is possible to follow the route of the pipeline, and continuously to monitor its potential. From the variations in the pipe potential, the adequacy of protection can be determined.

The above-described systems of surveying protected pipelines may be used where the cathodic protection is provided by a combination of impressed current and sacrificial anodes. Here, however, relatively large return currents flow in the pipeline, and consequently, in order to ensure that no appreciable voltage drop occurs in the metal of the pipeline between the position of the sacrificial anode and the point on the pipe being scanned at a particular instant by the test electrode(s), these anodes need to be relatively closely spaced.

Since the protection of the pipeline does not, in this case, rely entirely upon the sacrificial anodes, the latter may be made to have potentials much closer to the pipe potential than before. It would be possible to make the anodes so as to have a potential in seawater corresponding to the potential required of the pipe for proper protection and then it would be possible to scan the pipeline with the test electrode and detect any difference in the water potential adjacent the low voltage anodes and adjacent other parts of the pipe.

It would even be possible to make the "anode" potential less than the pipe potential though this would cause the "anode" to attract much more current and thus reduce the cathodic protection on the pipe.

I claim:

1. A method of surveying a cathodically protected metallic structure at least partly immersed in a liquid without making direct electrical contact with said metallic structure, the metallic structure having electrically connected thereto a metallic element of known electrolytic potential relative to the liquid, the method comprising measuring the potential differences between a point in the liquid adjacent the metallic element, and test points in the liquid adjacent the metallic structure, and determining the varying level of protection about the structure from the variations between the said potential differences.

2. A method according to claim 1 wherein to determine said potential differences a first test electrode is placed at said point adjacent said metallic element, and a second test electrode is placed at said points adjacent said various parts successively, and the potential difference between said first and second electrodes is monitored.

3. A method according to claim 1 wherein the metallic element is one of a plurality of sacrificial anodes attached to and spaced longitudinally of an elongate underwater structure, such as an undersea pipeline.

4. A method according to claim 1 including determining the potential of the pipe, at each of said various test points, relative to the liquid by subtracting from a predetermined potential difference derived from the said known electrolytic potential, the corresponding value of said potential difference in the liquid, and comparing the determined value of said potential with a predetermined value associated with minimum acceptable protection.

5. A method according to claim 1 wherein the changes in the potential differences between a reference electrode in the liquid remote from the structure and test electrode means which is moved about the structure, from a first value when said test electrode is adjacent the metallic element, and a changing second value when the test electrode is adjacent the respective test points, are monitored.

6. A method according to claim 5 wherein a peak in the potential difference between the test electrode means and the reference electrode occurs when the said test electrode means is adjacent the metallic element, and this peak value is used to determine, by subtraction, the required potential difference in the liquid as the test electrode means moves about the structure.

7. A method according to claim 6 wherein the metallic element is one of a plurality of sacrificial anodes attached to and spaced longitudinally of an elongate underwater structure, such as an undersea pipeline.

8. A method according to claim 7 wherein the test electrode means and the reference electrode are towed by a vessel moving on the surface of the water.

9. A method according to claim 8 wherein the test electrode means comprise a single test electrode towed by the vessel along the elongate underwater structure.

10. A method according to claim 8 wherein the test electrode means comprise a plurality of test electrodes towed in parallel along the elongate underwater structure by the vessel, and spaced apart transverse to the direction of travel of the vessel.

11. A method according to claim 10 wherein the varying potential of each test electrode relative to the reference electrode is monitored, and an estimate of the potential at the surface of the structure is derived from these potentials.

12. A method according to claim 11 wherein an estimate of the positions of the test electrodes relative to the elongate underwater structure is also derived, and the vessel is steered to reduce any deviation of said estimated positions from a symmetrical spacing about the line of the elongate structure.

13. A method according to claim 11 wherein the said potentials of the test electrodes relative to the reference electrode are visually displayed simultaneously on a single screen in analogue form.

14. A method according to claim 10 wherein the time-varying potential of each test electrode relative to the reference electrode is recorded in permanent form.

* * * * *